(12) United States Patent
Malek et al.

(10) Patent No.: US 7,187,978 B2
(45) Date of Patent: Mar. 6, 2007

(54) METHOD AND APPARATUS FOR PROGRAMMING AN IMPLANTABLE MEDICAL DEVICE

(75) Inventors: Shahram Malek, Plymouth, MN (US); Mark A. Christopherson, Shoreview, MN (US); Steven Goetz, Brooklyn Center, MN (US); John Grevious, Minneapolis, MN (US); David W. Lee, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 186 days.

(21) Appl. No.: 10/002,328

(22) Filed: Nov. 1, 2001

(65) Prior Publication Data

US 2003/0171789 A1 Sep. 11, 2003

(51) Int. Cl.
*A61N 1/08* (2006.01)

(52) U.S. Cl. ...................................... 607/59

(58) Field of Classification Search ............ 607/32–60, 607/30
See application file for complete search history.

(56) References Cited

U.S. PATENT DOCUMENTS

| | | | |
|---|---|---|---|
| 5,438,990 A | 8/1995 | Wahlstrand | |
| 5,662,691 A | 9/1997 | Behan et al. | |
| 5,683,432 A | 11/1997 | Goedeke | |
| 5,716,384 A | 2/1998 | Snell | |
| 6,067,474 A * | 5/2000 | Schulman et al. | |
| 6,381,496 B1 * | 4/2002 | Meadows et al. | 607/59 |
| 6,516,227 B1 | 2/2003 | Meadows et al. | |
| 6,580,948 B2 | 6/2003 | Haupert et al. | |
| 6,662,052 B1 * | 12/2003 | Sarwal et al. | 607/59 |
| 6,738,670 B1 * | 5/2004 | Almendinger et al. | 607/60 |
| 2001/0003799 A1 | 6/2001 | Boveja | |

OTHER PUBLICATIONS

International Search Report mailed Oct. 9, 2003.

* cited by examiner

*Primary Examiner*—Scott M. Getzow
(74) *Attorney, Agent, or Firm*—Banner & Witcoff, Ltd.

(57) ABSTRACT

A method and system for programming settings of a medical device surgically implanted within a body of a patient. The system comprises a physician programmer, a patient programmer, an external neural stimulator, and a telemetry component being in communication with the implanted medical device, the external neural stimulator, and the physician programmer. The implantable medical device may be programmed using a two-phase process, a screening phase and an implant phase. During the screening phase, the physician and patient programmers may be used to roughly test the parameters of the stimulation to determine that the treatment therapy is efficacious. During the implant phase, the same physician and patient programmers may be used to fine tune the parameters of the stimulation.

36 Claims, 14 Drawing Sheets

502

508   503   507

504  517

505

METHOD AND APPARATUS FOR PROGRAMMING AN IMPLANTABLE MEDICAL DEVICE

FIELD OF THE INVENTION

This invention relates to systems for physician/patient programming devices for implantable medical devices, and more particularly relates to a wireless programming system having uniform interfaces.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

These devices may provide treatment therapy by delivering electrical stimulation or drugs to various portions of the body. In the case of providing electrical stimulation, an implantable neurostimulator (INS) (also known as an Implantable Pulse Generator ((IPG)) is implanted within the body. The INS is coupled to one or more electrodes that provide electrical energy to select portions of the body. In the case of providing drugs, a pump is implanted within the body The pump is coupled to a catheter that delivers drugs to select portions of the body.

When these implantable devices are implanted within the body, they must first be programmed to provide the desired treatment therapy. In present systems, the programming process usually involves two phases—a screening phase and an implant phase.

In the screening phase, the implanted system is tested to determine the amount of stimulation or drug that is necessary, to adjust the treatment parameters, and determine whether the therapy is efficacious. As shown in FIG. 1, a screener 110 is used by both the patient 115 and the physician. The screener 110 is generally hardwired to the implanted device such as a stimulation lead and has a plurality of controls 120 for adjusting the settings of the implanted device.

In the implant phase, the implanted device 210 is fully implanted within the body of the patient 115. As shown in FIG. 2, a physician programmer 230, typically a computer with associated electronics, is used to program and subsequently adjust the settings of the implanted device. The physician programer 230 is coupled to a telemetry unit 240 via a cable 235. The patient 115 may also adjust the settings of the implanted device 210 using a patient programmer 220 that communicates with the implanted device 210 via telemetry. During the implant phase, the physician or patient may seek to adjust settings of the treatment therapy for any number of reasons including, for example, to fine tune the therapy, to account for changes in the disease being treated, or to account for migration of the implanted lead or catheter.

Known systems for programming a medical device have a number of disadvantages. For example, both the physician and the patient must learn to use two separate devices, namely the screener and the physician/patient programmer. This requires additional learning time and requires that the physician or patient relearn how to use their respective programming devices. More importantly, settings that were made by the screener during the screening phase must be manually re-entered during the implant phase into the medical device using the physician programmer or the patient programmer. Not only does this unnecessarily waste valuable physician time, it can also result in human error in re-entering the settings.

The screener of the prior art also is also problematic. Since the screener uses different circuitry to provide the stimulation energy, the stimulus provided by the screener during the screening phase may not be identical to the stimulus provided by the implanted device. Thus, any settings made by the screener may require quite different settings by the implanted device. In a worst case, the screener settings may even go beyond the capabilities of the implanted device. This may then require the risk of a second surgical procedure to remove the implanted device and leads from the patient. Further, screeners typically have coarse knobs to control stimulus settings and, as a result, they don't always give precise stimulus settings. Even further, most screeners require sterile cables to go from the sterile field to the screener and the screener itself is not sterilize-able. The present invention overcomes these and other disadvantages of the prior art.

BRIEF SUMMARY OF THE INVENTION

According to a preferred embodiment, a programming system of the present invention generally includes a hand-held physician programmer, a hand-held patient programmer, an external neural stimulator (ENS), and an implantable device. These units permit testing of an implanted medical device and allow the patient/physician to adjust settings of the treatment therapy to achieve optimal efficacy. The implantable device maybe, for example, an internal neural stimulator (INS) coupled to one or more leads, a drug pump coupled to one or more catheters, or a combination INS and pump. The system of the present invention may be implemented under a two-phase process: (1) a screening phase; and (2) an implant phase. First, during a screening phase, the ENS is coupled directly to the implanted leads. The physician and optionally the patient programmers may be used to program the ENS with the treatment parameters and to test the implanted leads to ensure that the implants have been properly positioned to provide the necessary treatment therapy. In addition, parameters of the stimulation can be tested to ensure that the treatment therapy is efficacious. Second, during the implant phase, the electrodes are coupled directly to the INS and the INS is programmed with the settings that were established for the ENS. During this phase, the parameters of the INS may need to be changed for any number of reasons, including, for example, fine-tuning of the treatment therapy, a change in patient conditions, and migration of the lead from the desired treatment area. Notably, the same programming units that were used by the physician and the patient, respectively, during the screening phase are used again during the implant phase. Advantageously, the patient and physician only need to learn to use one programming device. In addition, the wireless programming devices can be more conveniently handled.

BRIEF DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

The system of the present invention may be implemented for a two-phase implant process.

Figure 1:
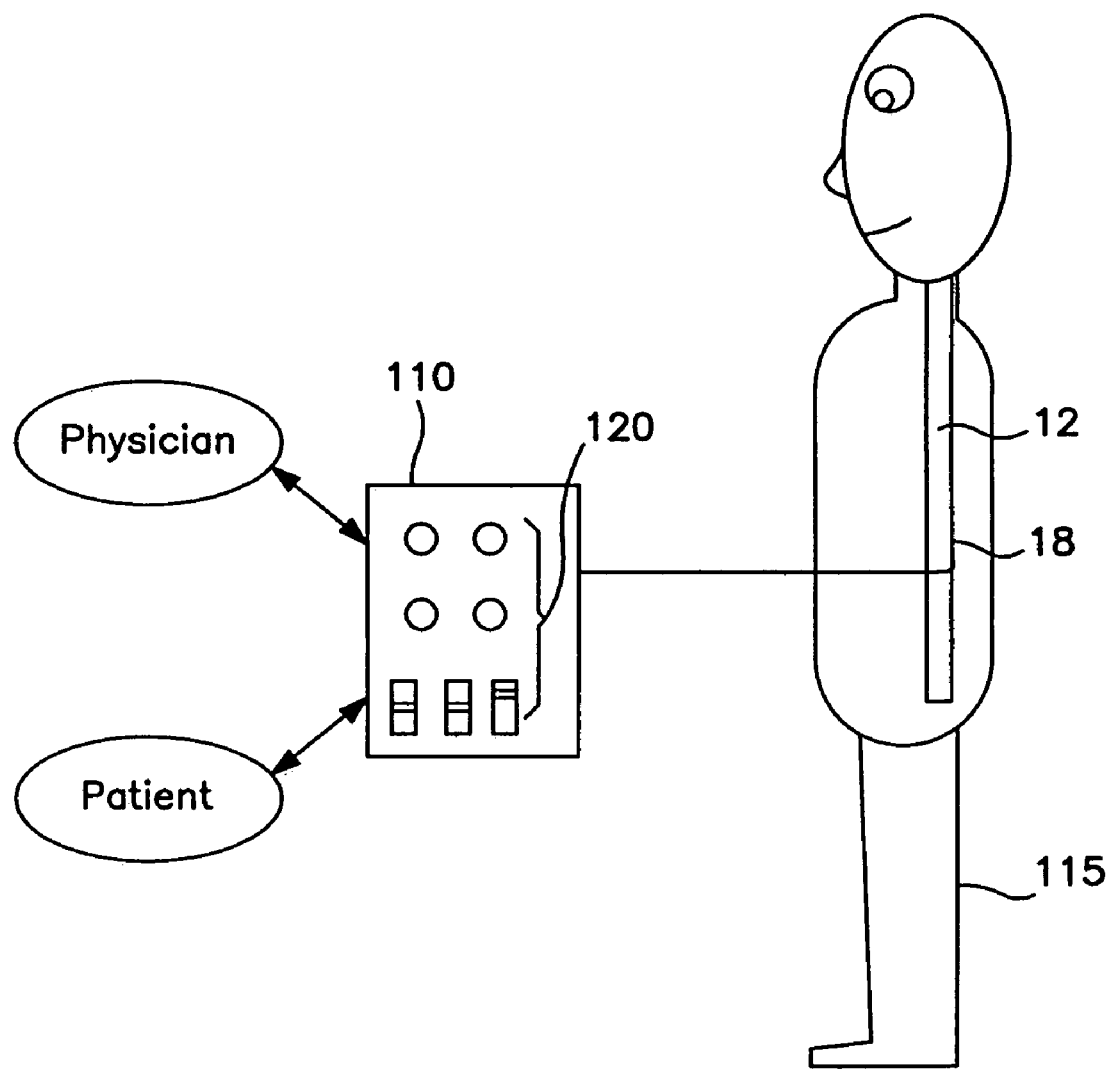
FIG. 1 is a schematic diagram of a screener as used in the screening phase of the prior art.
Figure 2:
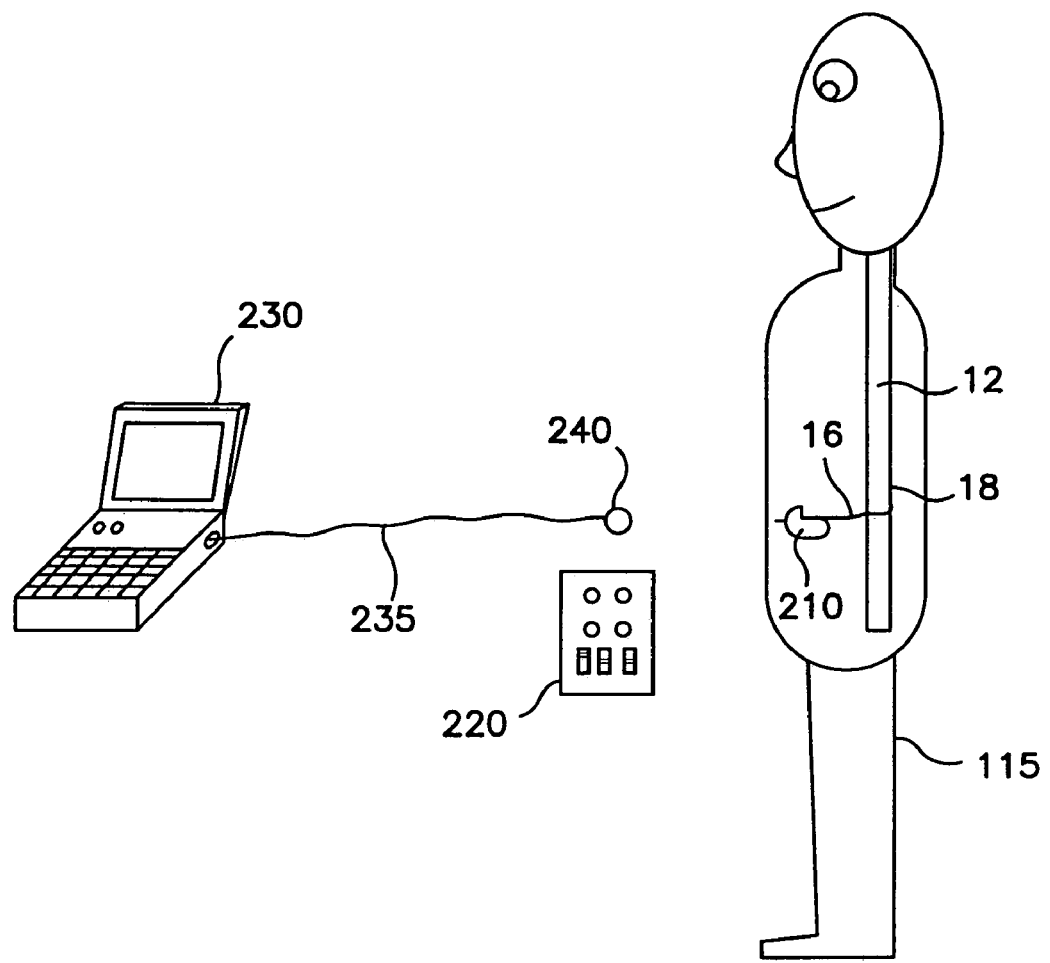
FIG. 2 is a schematic diagram of the physician and patient programmers as used in the implant phase of the prior art.
Figure 3A:
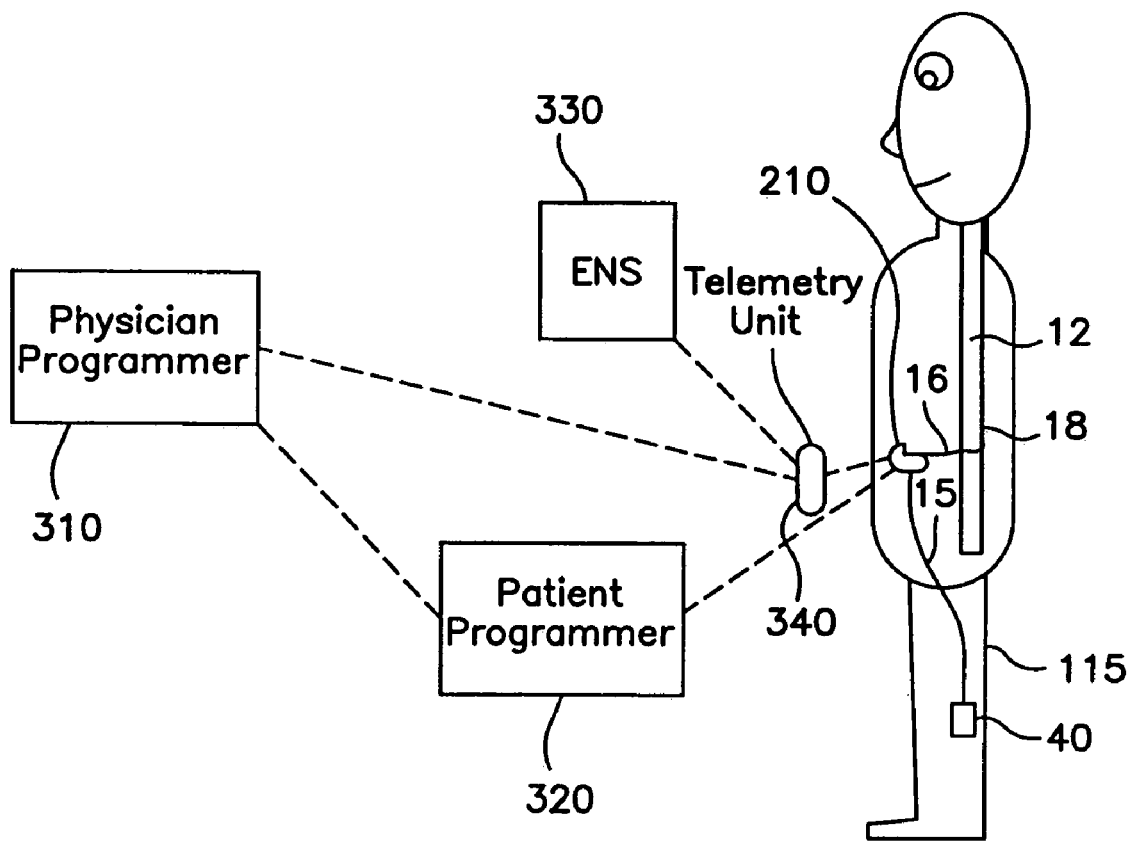
FIGS. 3A–3C are schematic diagrams of a programming system depicting the communications link between an external neural stimulator, an implantable signal generator, a physician programmer, and a patient programmer in accordance with a preferred embodiment of the present invention.
Figure 3B:
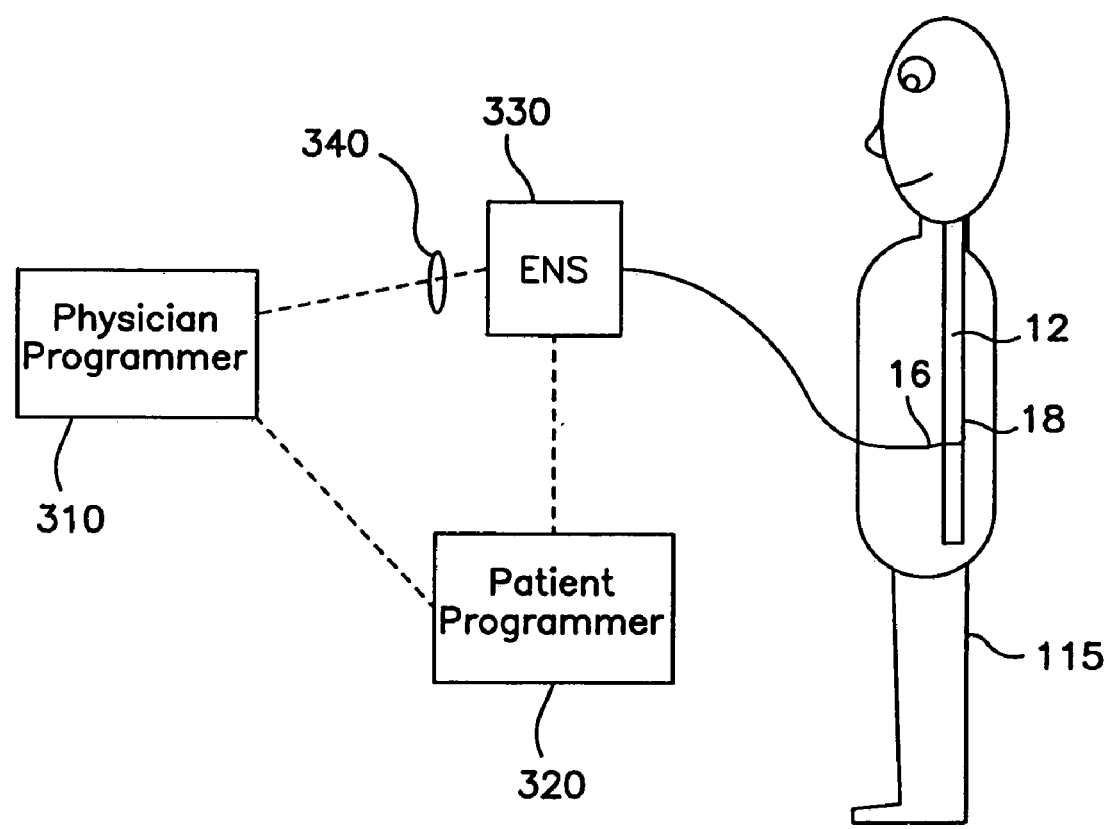
Figure 3C:
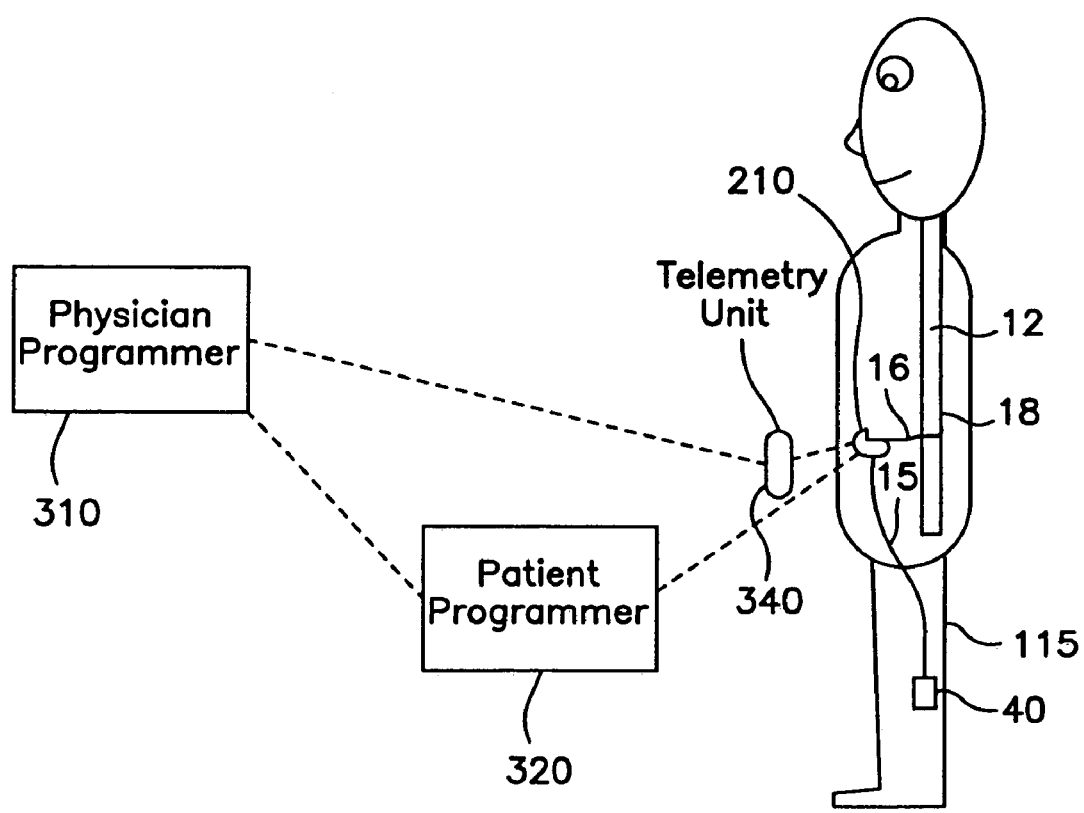

FIGS. 3A–3C illustrate the configuration of the components of the present invention during the various phases of implanting the medical device. Although the preferred embodiment of the present invention is shown for use with an implantable electrical stimulation system, those skilled in the art will appreciate that the programming system of the present invention may also be used to program an implantable drug delivery system (FIG. 4, discussed herein), or even a combination electrical stimulation/drug delivery system.

Referring to FIG. 3A, the programming system of the present invention generally includes a hand-held physician programmer 310, a remote telemetry unit 340, a hand-held patient programmer 320, an external neural stimulator (ENS) 330, an implantable neural stimulator (INS) 210, and one or more leads 16. These units permit testing of an implanted medical device and allow the patient/physician to adjusting settings of the treatment therapy. Advantageously, the same programming units that were used by the physician and the patient, respectively, during the screening phase are used again during the implant phase. Each of these components may be powered by separate power sources such as a battery. The implantable neural stimulator 210 may be placed in any number of locations within the body, including the abdominal region. The implantable neural stimulator 210 is coupled to a lead 16 that terminates in one or more electrodes 18 that deliver the desired stimulation therapy to the body. In the exemplary embodiment of FIG. 3A, the electrodes 18 are positioned to stimulate a spinal cord 12 of a patient 115. The implantable neural stimulator 210 may also have one or more sensors 40 to provide closed-loop feedback control.

Figure 4:
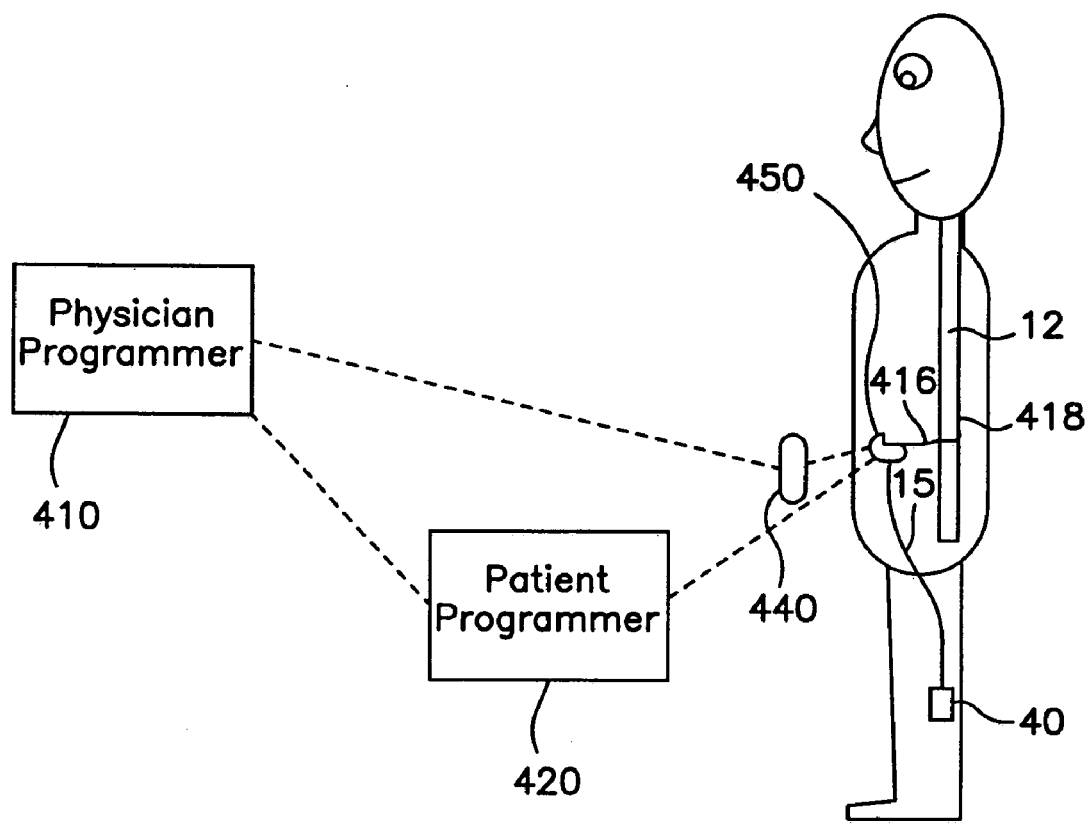
FIG. 4 is a schematic block diagram of a programming system for implantable pumps in accordance with another preferred embodiment of the present invention.

The INS 210 is typically a signal generator having a processor or like circuitry. For example, signal generator may take the form of commercially available signal generators like Itrel7, X-trel7 or Mattrix7 (manufactured by Medtronic, Inc. of Minneapolis, Minn.), which are incorporated by reference. Where the implanted medical device is a drug delivery system, as shown in FIG. 4, the device generally consists of a drug pump 450 coupled to one or more catheters 416 having one or more drug delivery ports 418 on the distal ends. Drug pump 450 may take the form of the device shown in U.S. Pat. No. 4,692,147 (Duggan), assigned to Medtronic, Inc., Minneapolis, Minn., and commercially available as the Synchromed7 infusion pump, both of which are incorporated by reference.

The operation of implanted medical devices 210 and 450 is generally well-understood by those skilled in the art. Those skilled in the art will therefore appreciate that the implanted medical device 210 or 450 for use with the present invention can take many forms and embodiments. For example, the implanted medical device 210 or 450 maybe a system that provides a combination of electrical stimulation and drug delivery. Those skilled in the art will also appreciate that the programming system of the present invention is suited for use with any known or future developed implantable medical devices. The particulars of the individual components of the programming system of the present invention are discussed in further detail below.

FIG. 3B depicts the configuration of the programming system during the screening phase in accordance with a preferred embodiment. During the screening phase, the ENS 330 is hardwired directly to the proximal ends of the implanted leads 16. The physician and optionally the patient programmers 310 and 320 may be used to program the ENS 330 with initial treatment parameters. The ENS 330 may be used to test the implanted leads 16 to ensure that the leads 16 have been properly positioned to provide the necessary treatment therapy. In addition, ENS 330 tests the initial treatment parameters to ensure that the treatment therapy is efficacious.

In accordance with the present invention, a bi-directional communications link exists between the physician programmer 310 and the ENS 330 to enable the physician programmer 310 to program the ENS 330 with the treatment parameters via the bi-directional communications link. The treatment parameters may be provided singly or in a batch, or the parameters may be provided one at a time in a real-time interactive mode. The bi-directional communications link enables the physician programmer 310 to provide to the ENS 330 configuration information for the type of the INS 210 that is to be implanted. The ENS 330 may thereby be configured to provide stimulation therapy in accordance with the type of INS 210 that is implanted. The physician programmer 310 may also upgrade the software or operating system of the ENS 330 via this bi-directional communications link.

In addition, this bi-directional communications link enables the ENS 330 to provide final treatment parameter settings to the physician programmer 310, thereby allowing the physician programmer 310 to program the INS 210 using these final treatment parameters. The bi-directional communications link also enables the ENS 330 to provide information to the physician programmer 310 including, but not limited to, parameter settings, user-entered data, patient diagnostic data, system diagnostic data, device usage data, data regarding the last session between the physician programmer 310 and the ENS 330, the state of the ENS 330, configuration of the INS 210 (e.g., simple or complex patient user interface), and the like. Finally, the bi-directional communications link provides an indication that a viable communications link exists between the physician programmer 310 and the ENS 330.

In the preferred embodiment, this bi-directional communications link is provided by the remote telemetry unit 340. Those skilled in the art will appreciate that the functionality of the remote telemetry unit 340 may be implemented within, for example, the physician programmer 310 and the ENS 330. As preferred, the physician programmer 310 communicates with the remote telemetry unit 340 via high-power signaling, which then communicates with the ENS 330 via low-power RF or IR signaling, or direct wire communication. Low-power signaling generally will allow a separation of 2 to 6 inches between the communicating devices. High-power signaling, on the other hand, allows for greater separation between the communicating devices, up to several meters. Advantageously, this type of signaling allows the physician programmer 310 to be located farther away from the patient 115 as long as the remote telemetry unit 340 is positioned relatively close to the INS 210.

The patient programmer 320 is generally not used during the screening phase, however, if used, it communicates with the ENS 330 via low-power RF or IR signal, or direct wire communication. The patient programmer 320 would control the ENS 330 preferably for more limited purposes than that permitted for the physician programmer 310. Again, although not required, the patient programmer 320 communicates with the ENS 330 via the remote telemetry unit 340. Using the physician programmer 310 and, optionally, the patient programmer 320, the ENS 330 maybe programmed with initial parameter settings. The ENS 330 may also provide certain diagnostic information back to the programmer 310 including, for example, parameter settings (e.g., stimulation frequency, stimulation pulse amplitude, stimulation pulse width, electrode configuration, etc.), patient diagnostic data (e.g., usage data), system diagnostic data (e.g., battery status, estimated longevity of implanted device, lead system integrity, load impedance, etc.), data on device usage, data regarding the last programmer/ENS session, the state of the device, configuration of the INS 210 (e.g., simple or complex patient user interface), whether a valid communication channel exists, and the like. This information may also be provided from the INS 210 to the programmer 310 during the implant phase (discussed herein). The programmer 310 may also telemetrically upgrade ENS functionality.

Further, the physician programmer 310 may communicate with the patient programmer 320 using low-power RF or IR signaling. This communication ability allows the physician and patient programmer 310 and 320 to synchronize parameters values programmer in the ENS 330. This communication ability also allows the physician programmer 310 to perform any number of functions including, for example, upgrade the functionality of the patient programmer 320 if necessary, obtain system diagnostic and hardware revision data from the patient programmer 320, power source status of the patient programmer 320, configure the patient programmer 320 to operate with the specific ENS 330 or INS 210.

Once the ENS 330 is configured with appropriate stimulation settings, the ENS 330 maybe replaced with the INS 210. FIG. 3C illustrates the communications capabilities between the ENS 330, the physician programmer 310, and the patient programmer 320 during the implant phase in accordance with a preferred embodiment. During the implant phase, the electrodes are coupled directly to the INS 210 and the INS 210 is programmed with the settings that were established for the ENS 330. The programmed settings that were transferred from the ENS 330 to the physician programmer 310 and/or the patient programmer 320 may then be transferred from the physician programmer 310 and/or the patient programmer 320 to the INS 210. Advantageously, since manual re-entering of parameter information is not required on the programmers 310 and 320, risk of operator error is eliminated. Further, the implant procedure is simplified and streamlined. During this phase, the parameters of the INS 210 may need to be changed for any number of reasons, including, for example, fine-tuning of the treatment therapy, a change in patient conditions, and migration of the lead from the desired treatment area. The physician programmer 310 or patient programmer 320 may communicate with the INS 210 via the remote telemetry unit 340 using low-power RF or IR signaling.

The above-described inter-connectivity of the components of the programming system allows the physician to program the settings of the ENS 330 and INS 210 using a single device, namely the physician programmer 310. Optionally, the system also allows the patient 115 to program the settings of the ENS 330 and INS 210 using a single device, namely the patient programmer 320. The following table identifies which products can interact with which other products in accordance with a preferred embodiment:

|  | INS | ENS | Physician Programmer | Patient Programmer | Patient Recharge |
|---|---|---|---|---|---|
| INS |  |  | √ | √ | √ |
| ENS |  |  | √ | √ |  |
| Physician Programmer | √ | √ |  | √ |  |
| Patient Programmer | √ | √ | √ |  | √ |
| Patient Recharge | √ |  |  | √ |  |

The programming units 310 and 320 communicate with the ENS 330 as follows. Setting control signals from the physician programmer 310 are delivered to the ENS 330 when the two devices are physically within the range allotted by the low-power signaling. Accordingly, ENS 330 may have one or more flanges or other connection device on its dorsal side to allow connection with mating flanges on the ventral side of the remote telemetry unit 340. This mating capability ensures that the components will be in close proximity of each other to allow the exchange of data and control signals. It will be readily apparent that any other technique may be used to maintain the components in close proximity of each other.

Optionally, setting control signals from the patient programmer 320 are delivered directly to the ENS 330 as long as the ENS 330 and the patient programmer 320 are physically within the range allotted by the low-power signaling. Optionally, ENS 330 may have one or more flanges one its dorsal side to allow connection with mating flanges on the ventral side of the remote telemetry unit 340.

Figure 5A:
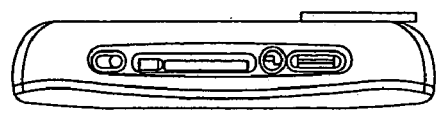
FIGS. 5A–5B are multiple view diagrams of the physician programmer in accordance with the preferred embodiment of the present invention.
Figure 5A:
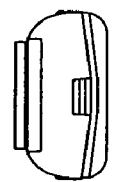
Figure 5A:
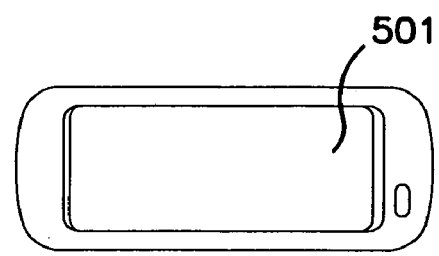
Figure 5A:
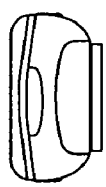
Figure 5A:
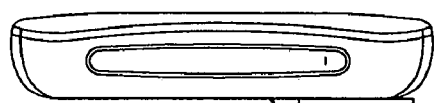
Figure 5A:
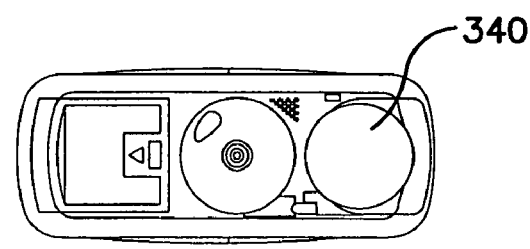
Figure 5B:
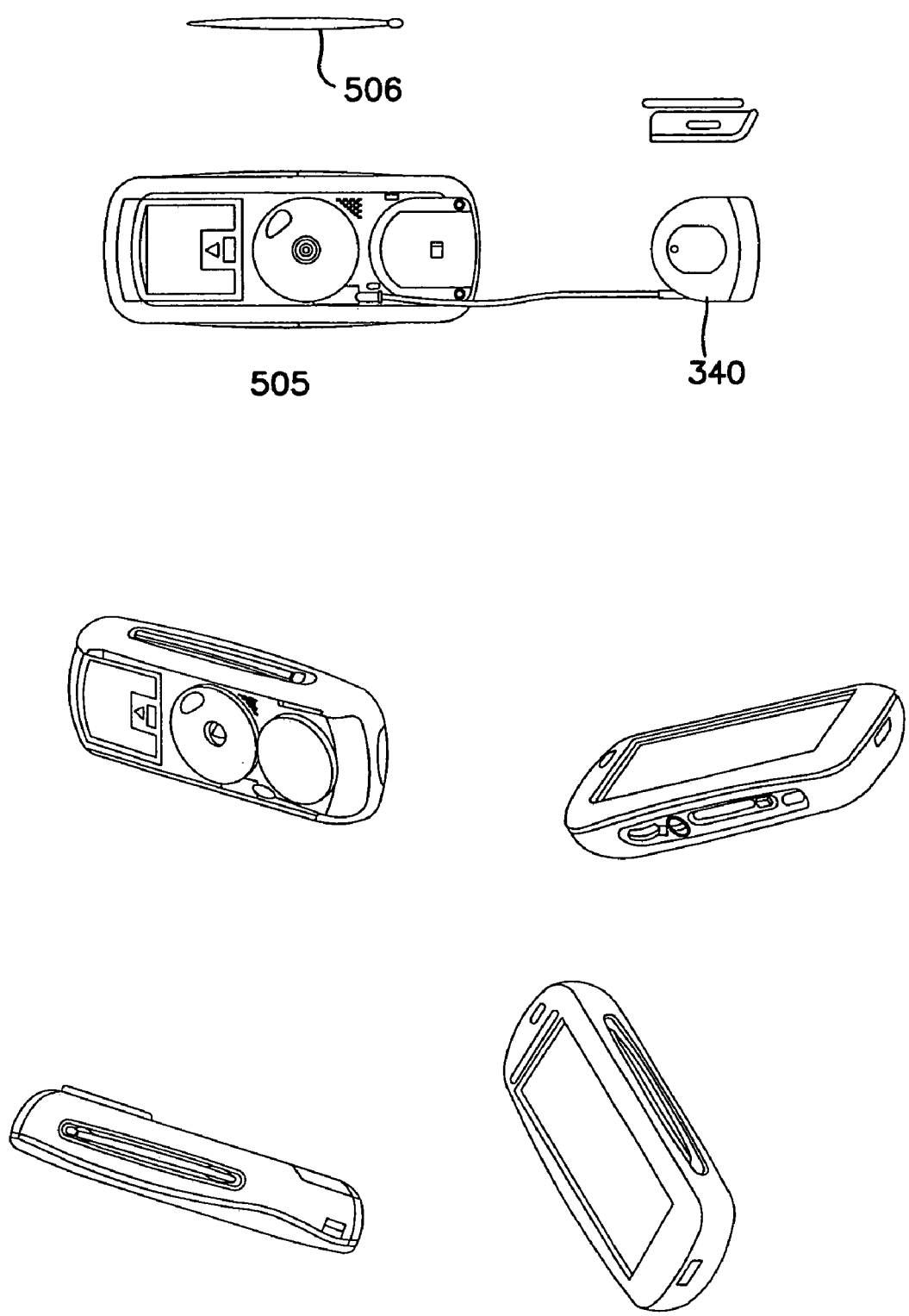
Figure 5C:
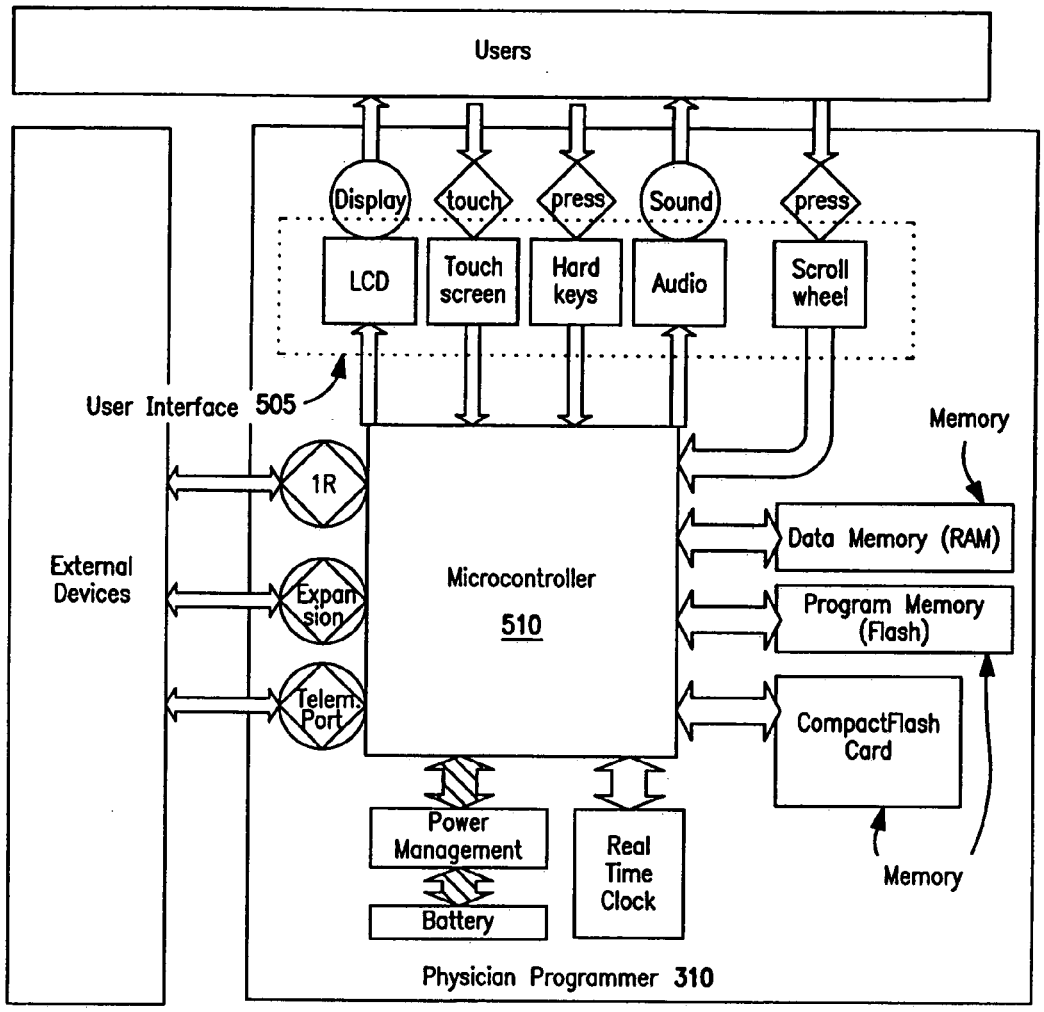
FIG. 5C is a block diagram of a hand-held physician programmer in accordance with the preferred embodiment of the present invention.

FIG. 5A depicts views of the physician programmer 310 including a front view, 503, a top view 502, a bottom view 504, a back view 505, a left side view 508, and a right side view 507. The physician programmer 310 is preferably a portable computing device having a user interface. The user interface preferably includes a screen display 501 that is touch sensitive to a pointing device 506, similar to that of Personal Digital Assistants (PDA) available today. On the dorsal side 517 of the physician programmer 310 is an area to receive and hold the remote telemetry unit 340. FIG. 5B illustrates how remote telemetry unit 340 is insertable within a dorsal side 517 of the physician programmer 310. FIG. 5C depicts the general componentry of the physician programmer 310, which includes a user interface 505, a processor 510, a transmitter 515, and a receiver 520. The application program software for handling the functionality of the programmer 310 discussed herein maybe stored in memory 525.

The physician programmer 310 acts as the control interface to both the ENS 330 and the INS 210, which is generally dictated by the computer software application in the phyician programmer. The software application generally has the following methods for implementing its control functionality: navigation methods; reporting methods; printing methods; data storage and transfer methods; data entry methods; methods to perform interrogation/review; methods to perform batch programming; user preferences; help methods; methods to resolve conflicts, and the like.

Figure 6:
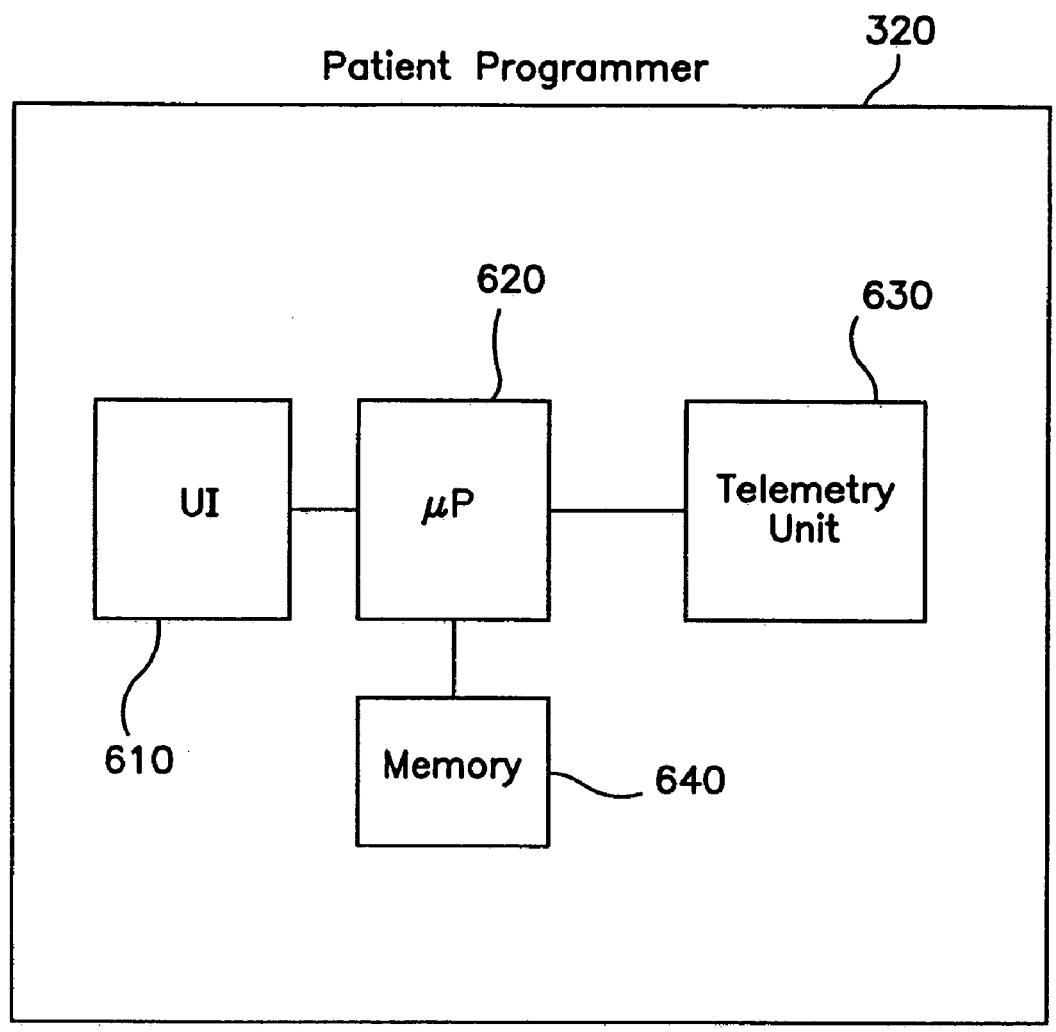
FIG. 6 is a block diagram of a hand-held patient programmer in accordance with the preferred embodiment of the present invention.

As shown in FIG. 6, the patient programmer 320 is also preferably a computing device, such as a portable computer, having a user interface. Patient programmer 320 is similar to physician programmer 310 except that it has limited functionality. Typically, patient programmer 320 will be limited such that the patient may adjust settings of the implanted medical device 210 or 450 only within a range, such as that specified by the treating physician. The patient programmer 320 includes similar circuitry as that of the physician programmer 310 and also preferably includes an internal telemetry unit 630 that is similar to the remote telemetry unit 340.

Figure 7:
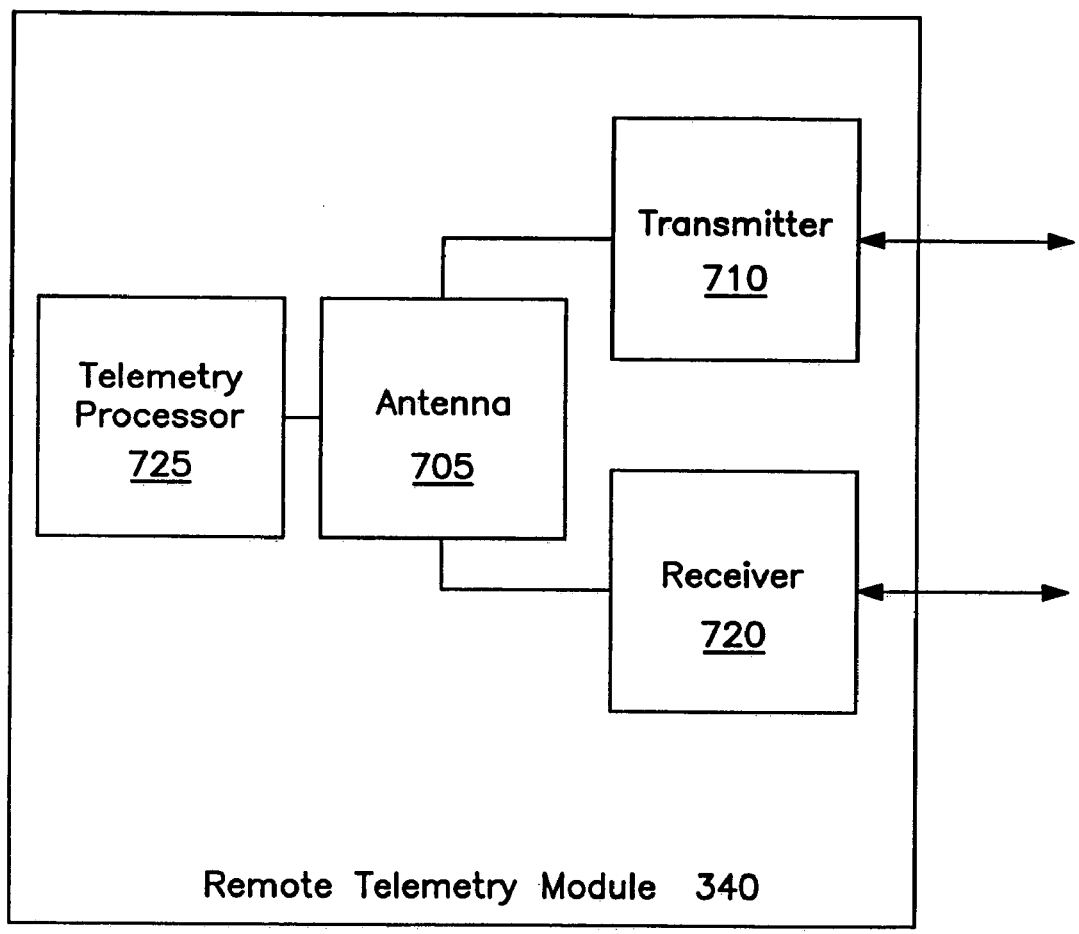
FIG. 7 is a block diagram of a remote telemetry unit in accordance with the preferred embodiment of the present invention.

As shown in FIG. 7, the remote telemetry unit 340 is a relatively small device used to conveniently provide communication between the physician programmer 310 and the implanted medical device 210 or 450. Remote telemetry unit 340 generally includes a telemetry coil 705, a receiver 710, a transmitter 715, and a telemetry processor 720. Telemetry is preferably conduced at a frequency in the range from about 150 KHz to 200 KHz using a medical device protocol such as described in U.S. Pat. No. 5,752,977 "Efficient High Data Rate Telemetry Format For Implanted Medical Device" issued to Grevious et al. (May 19, 1998). The telemetry coil 705 can be located inside the housing of the remote telemetry unit 340 or attached to the outside of the housing. The receiver 710 provides a digital pulse representing the Radio Frequency (RF) modulated signal received from the physician programmer 310 and the implanted medical device 210 or 450. The transmitter 715 generates an RF modulated signal from the digital signal generated by the telemetry processor. The telemetry processor 720 can be a state machine configured on an ASIC with the logic necessary to decode telemetry signal during reception. The telemetry processor 720 also provides the logic necessary during transmission.

Figure 8:
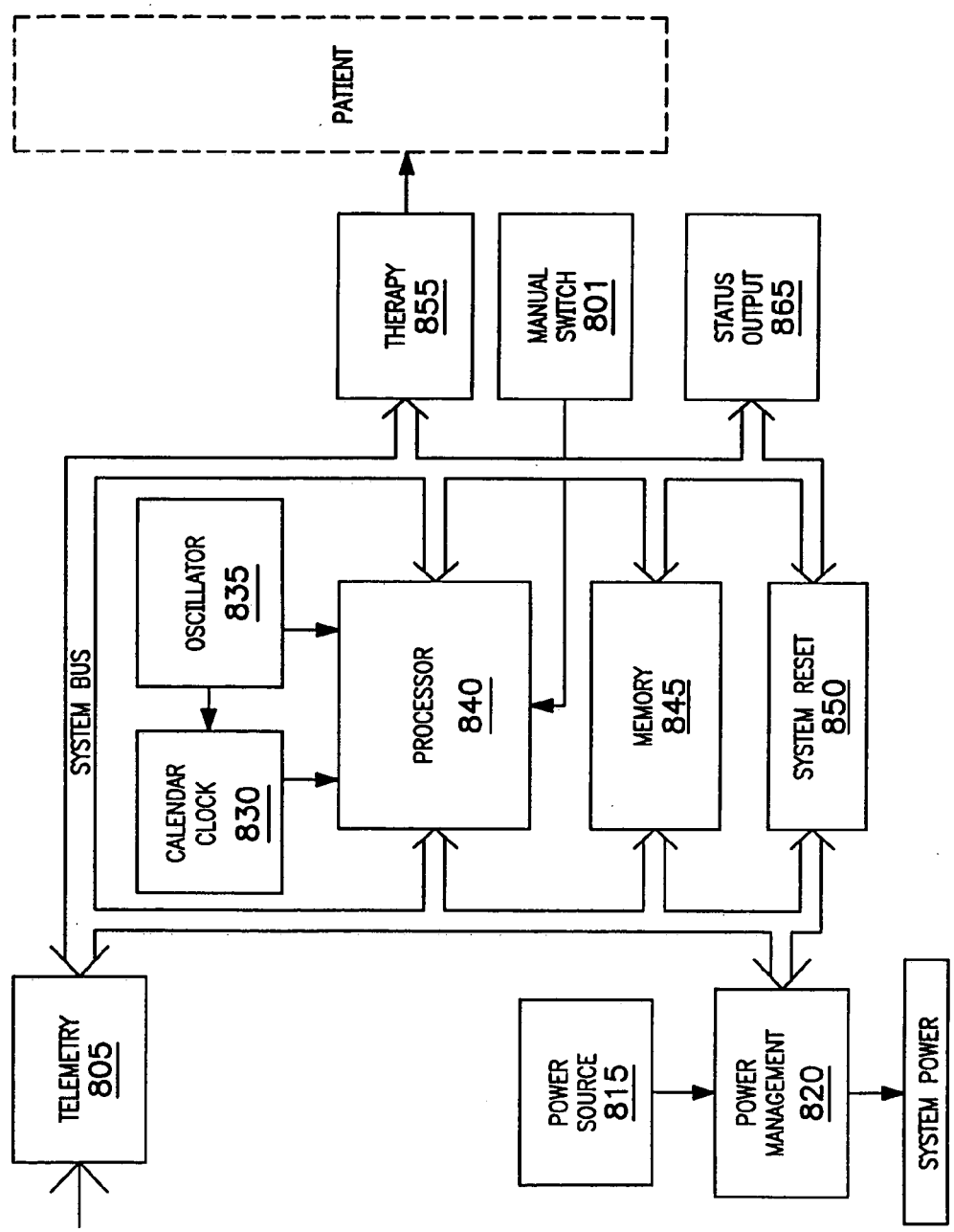
FIG. 8 is a block diagram of an external neural stimulator in accordance with the preferred embodiment of the present invention.

As shown in FIG. 8, the ENS 330 is similar to the INS 210 in terms of componentry except that it is an external device. The ENS 330 is intended to provide temporary stimulation for trial screening prior to implantation of the INS 210. The ENS 330 will emulate all of the functions of the INS 210 along with memory. The ENS has a means to mechanically link to the telemetry module 340.

Referring still to FIG. 8, the ENS 330 generally includes a processor 840 with an oscillator 835, a calendar clock 830, memory 845, system reset 850, a telemetry module 805, a recharge module 810, a power source 815, a power management module 820, a therapy module 855, a power source 815, a power management module 820, a manual switch 801 (to manually disable operation of the ENS 330), and a status output 865. Other components of the ENS 330 can include, for example, a diagnostics module (not shown). All components except the power source can be configured on one or more Application Specific Integrated Circuits (ASICs) or may be one or more discrete components, or a combination of both. Also, all components except the oscillator 835, the calendar clock 830, and the power source 815 are connected to bi-directional data bus that is non-multiplexed with separate address and data lines.

The processor 840 is synchronous and operates on low power such as a Motorola 68HC11 synthesized core operating with a compatible instruction set. The oscillator 835 operates at a frequency compatible with the processor 840, associated components, and energy constraints such as in the range from 100 KHz to 1.0 MHZ. The calendar clock 830 counts the number of seconds since a fixed date for date/time stamping of events and for therapy control such as circadian rhythm linked therapies. The memory 845 includes memory sufficient for operation of the ENS 330 and storage of a plurality of operating parameters. Memory 845 may include volatile Random Access Memory (RAM) for example Static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as the telemetry module 805, so the telemetry module 805 can request control of the data bus and write data directly to memory bypassing the processor 840. The system reset controls operation of ASICs and modules during power-up of the ENS 330, so ASICs and modules registers can be loaded and brought on-line in a stable condition.

The telemetry module 805 provides bi-directional communications between the ENS 330 and the programmers 310 and 320. The telemetry module 805 generally comprises a telemetry antenna 705, a receiver 720, a transmitter 710, and a telemetry processor 725. Telemetry modules 805 are generally known in the art-and are further detailed in U.S. Pat. No. 5,752,977, entitled AEfficient High Data Rate Telemetry Format For Implanted Medical Device@ issued to Grevious et al. (May 19, 1998), which is incorporated herein by reference in its entirety.

Figure 8A:
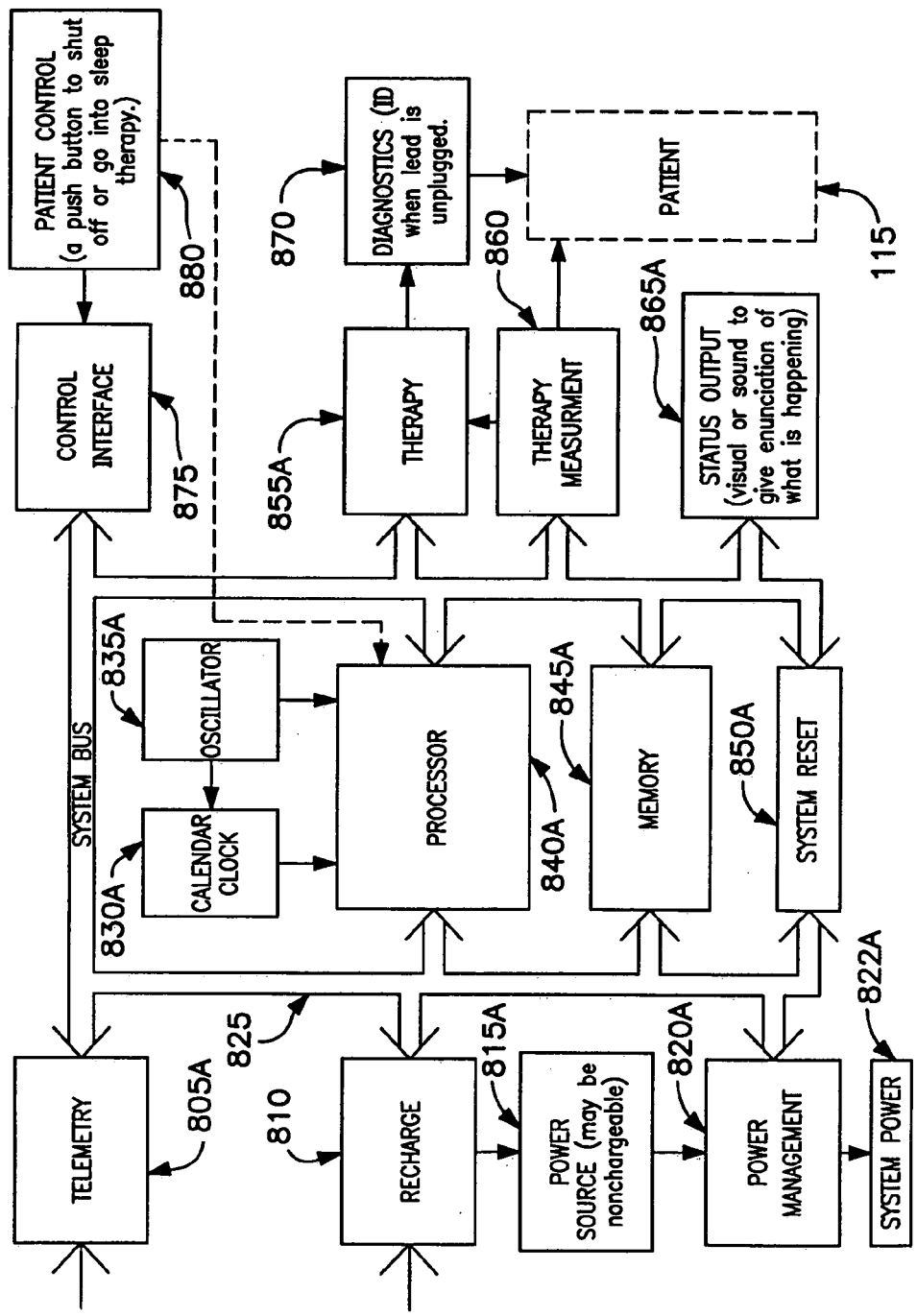
FIG. 8A is a block diagram of an implantable neural stimulator in accordance with the preferred embodiment of the present invention.

Those skilled in the art will appreciate that the ENS 330 may be configured in a variety of versions by removing modules not necessary for the particular configuration and by adding additional components or modules. As preferred, the ENS 330 accurately simulates the operation of the INS 210 and may be readily adjusted by the physician or the patent. The stimulation parameters set by the ENS 330 may adjusted using the physician programmer 310 (and optionally the patient programmer 320). As shown in FIG. 8A, the components of the ENS 330 are similar to those of the INS 210.

In another embodiment, ENS 330 need not be used. Instead, INS 210 may be used as an external device during the screening phase. When the parameters are properly set, the INS 210 may then be implanted within the patient 115.

As discussed above, the process for implanting a medical device is usually a two-phase process, a screening phase and an implant phase. The screening phase is a test phase that allows the physician and the patient to ensure that the implanted electrode has been properly positioned to provide the necessary treatment therapy. In addition, parameters of the stimulation can be tested to determine that the treatment therapy is efficacious. The implant phase takes place after the medical device has been fully implanted. During the implant phase, the parameters of the INS 210 may need to be changed for any number of reasons, including, for example, fine-tuning of the treatment therapy, a change in patient conditions, and migration of the lead from the desired treatment area. Notably, the same programming units that were used by the physician and the patient, respectively, during the screening phase are used again during the implant phase. Advantageously, the patient and physician only need to learn to use one programming device. Also, the programming devices can be more conveniently handled since the communications are wireless.

Figure 9:
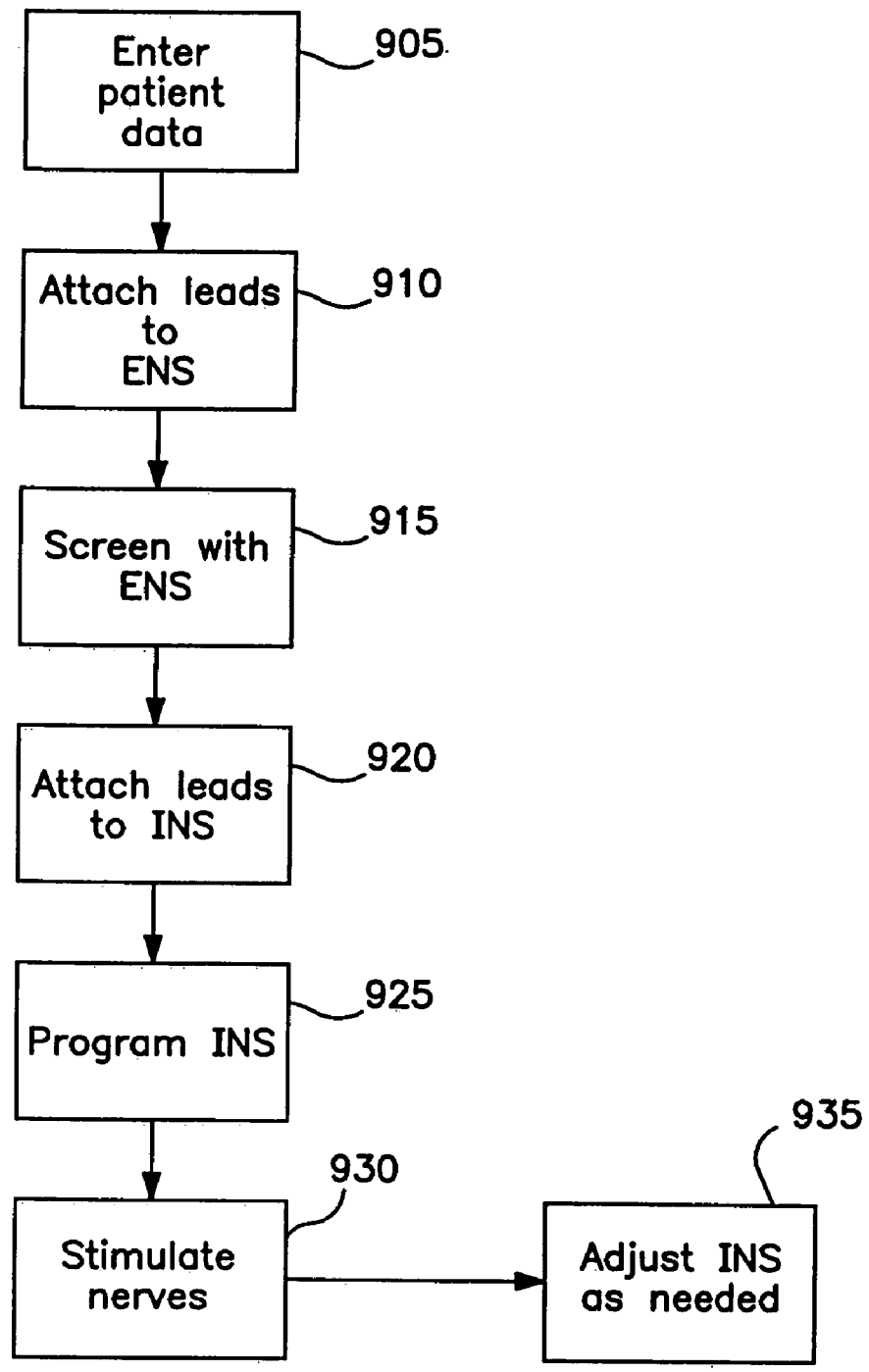
FIG. 9 is a flow chart depicting the programming process in accordance with the present invention.

FIG. 9 is a flow chart depicting the programming process during the screening and implant phases in accordance with the preferred embodiment of the present invention. At step 905, when the medical device is ready for implant within the patient body, patient record data is entered into the physician programmer 310. At step 910, the electrical leads 18 are implanted within the patient body by implanting the distal ends of the leads 18 (having the electrodes) near the desired treatment area within the body and by coupling the proximal ends of leads directly to the ENS 330. At step 915, the screening process is performed using the ENS 330. In the screening process, stimulation parameters are adjusted to ensure proper placement of the leads and to achieve optimal treatment efficacy. Settings adjustments that can be made include for example, pulse width, pulse amplitude, and pulse frequency. Where a plurality of electrodes is placed, the electric field may be steered to accurately focus the stimulation to the neural tissue of interest. Further, paired-pulsing techniques may be adjusted to achieve desired potential areas. As the settings of the ENS 330 are altered, these settings are provided to the physician programmer 310 so that the final settings may be used to program the INS 210 during the implant phases. As discussed previously, FIG. 3A depicts the programming system components during the screening phase.

At step 920, after the screening step has been performed, the leads 18 are disconnected from the ENS 330 and coupled directly to the INS 210. At step 925, the last settings from the ENS 330 are used to program the INS 210 with the appropriate stimulation parameters. In this regard, the settings from the ENS 330 are communicated to the physician and/or patient programmers 310 and 320 who then provide these settings to the INS 210. At step 930, the INS 210 provides the necessary stimulation therapy to the patient 115. At step 935, the physician and patient programmers 310 and 320 may be used to fine-tune the stimulation therapy of the INS 210 as needed. As discussed previously, FIG. 3C depicts the programming system components during the implant phase.

In an alternative embodiment, the present invention may be implemented within a drug delivery system. In this embodiment, as shown in FIG. 4, the programming system of the present invention generally includes similar components as before, namely a hand-held physician programmer 410, a remote telemetry unit 440, a hand-held patient programmer 420, and an implanted drug pump 450 coupled to one or more catheters 416. Each of the catheters 416 terminate with one or more drug delivery ports 418 on the distal ends of the catheters. Drug pump 450 may take the form of the device shown in U.S. Pat. No. 4,692,147 (Duggan), assigned to Medtronic, Inc., Minneapolis, Minn., and commercially available as the Synchromed7 infusion pump, both of which are incorporated by reference. Similar programming steps described above may thereby be taken to program the drug pump 450.

Advantageously under the present invention, the procedures for programming the implantable medical device are simplified. Both the patient and the physician may use a single interface (the patient programmer 320 and the physician programmer 310, respectively) to communicate with the implantable medical device. Further, the present invention eliminates the need for any hard wires as part of the programming system.

It will be appreciated that the present invention may be implemented using other embodiments. For example, one alternative embodiment is one where all of the components communicate using high-power signaling. Another alternative embodiment is the physician programmer 310 and the ENS 330 both having internal telemetry units, thereby eliminating the need for the remote telemetry unit 340. In another embodiment, the physician programmer 310 and the patient programmer 320 are the same device. Those skilled in the art recognize that the preferred embodiments maybe altered and modified without departing from the true spirit and scope of the invention as defined in the appended claims.

We claim:

1. A system for establishing therapy parameters of an implantable medical device comprising in combination:
   (a) at least one implantable lead;
   (b) an external neural stimulator capable of being coupled to the implantable lead to provide stimulation energy to the lead in accordance with initial therapy parameters;
   (c) a programmer having a user interface to allow entry of the therapy parameters by a user, wherein the programmer is configured to provide to the external neural stimulator configuration information for a type of an implantable neural stimulator that is to be implanted; and
   (d) a means for providing a bi-directional communications link between the programmer and the external neural stimulator to enable the programmer to program the external neural simulator with the therapy parameters via the bi-directional communications link and to enable the external neural stimulator to provide final therapy parameter settings to the programmer, whereby the programmer may then program an implantable neural stimulator using the final therapy parameters.

2. The system as claimed in claim 1, wherein the programmer is configured to provide the external neural stimulator with upgraded computer executable instructions.

3. The system as claimed in claim 1, wherein the external neural stimulator is configured to provide information to the programmer, wherein the information is selected from the group consisting of parameter settings, patient diagnostic data, system diagnostic data, data on device usage, data regarding the last programmer/ENS session, the state of the device, configuration of the INS 210, and whether a valid communication channel exists.

4. The system as claimed in claim 3, wherein the parameter setting information is selected from the group consisting of stimulation frequency, stimulation pulse amplitude, stimulation pulse width, and electrode configuration.

5. The system as claimed in claim 3, wherein the patient diagnostic data is usage data.

6. The system as claimed in claim 3, wherein the system diagnostic data information is selected from the group consisting of battery status, estimated longevity of implanted device, lead system integrity, and load impedance.

7. The system as claimed in claim 1, wherein the programmer is configured to determine that a viable communications link exists between the programmer and the external neural stimulator.

8. The system as claimed in claim 1, wherein the programmer is mechanically linked to the external neural stimulator.

9. The system as claimed in claim 1, wherein the programmer is a physician programmer.

10. The system as claimed in claim 1, wherein the programmer is a patient programmer.

11. A system for establishing therapy parameters of an implantable medical device comprising in combination:
    (a) at least one implantable lead;
    (b) an external neural stimulator capable of being coupled to the implantable lead to provide stimulation energy to the lead in accordance with initial therapy parameters;
    (c) a programmer having a user interface to allow entry of the therapy parameters by a user, wherein the programmer is further configured to provide to the external neural stimulator configuration information for a type of the implantable neural stimulator that is to be implanted;
    (d) a means for providing a bi-directional communications link between the programmer and the external neural stimulator to enable the programmer to program the external neural simulator with the therapy parameters via the bi-directional communications link and to enable the external neural stimulator to provide final therapy parameter settings to the programmer, whereby the programmer may then program an implantable neural stimulator using the final therapy parameters;
    (e) an implantable neural stimulator capable of being coupled to the implantable lead to provide stimulation energy to the lead; and
    (f) a means for providing a second communications link between the programmer and the implantable neural stimulator to enable the programmer to program the implantable neural simulator with the final therapy parameters via the second communications link.

12. The system as claimed in claim 11, wherein the programmer is configured to provide the external neural stimulator with upgraded computer executable instructions.

13. The system as claimed in claim 11, wherein the external neural stimulator is configured to provide information to the programmer, wherein the information is selected from the group consisting of parameter settings, patient diagnostic data, system diagnostic data, data on device usage, data regarding the last programmer/ENS session, the state of the device, configuration of the INS 210, and whether a valid communication channel exists.

14. The system as claimed in claim 13, wherein the parameter setting information is selected from the group consisting of stimulation frequency, stimulation pulse amplitude, stimulation pulse width, and electrode configuration.

15. The system as claimed in claim 13, wherein the patient diagnostic data is usage data.

16. The system as claimed in claim 13, wherein the system diagnostic data information is selected from the group consisting of battery status, estimated longevity of implanted device, lead system integrity, and load impedance.

17. The system as claimed in claim 11, wherein the programmer is configured to determine whether a viable communications link exists between the programmer and the external neural stimulator.

18. The system as claimed in claim 11, wherein the programmer is mechanically linked to the external neural stimulator.

19. The system as claimed in claim 11, wherein the programmer is a physician programmer.

20. The system as claimed in claim 11, wherein the programmer is a patient programmer.

21. A programmer for establishing therapy parameters of an implantable medical device comprising in combination:
    (a) a user interface to allow entry of the therapy parameters by a user; and
    (b) a bi-directional communications interface for communicating with an external neural stimulator, wherein the programmer is configured to program the external neural simulator with the therapy parameters, the programming including configuration information regarding a type of an implantable neural stimulator that is to be implanted and is further configured to receive final therapy parameter settings from the external neural stimulator, and wherein the programmer is further configured to program the implantable neural stimulator using the final therapy parameters.

22. The system as claimed in claim 21, wherein the programmer is a physician programmer.

23. The system as claimed in claim 21, wherein the programmer is a patient programmer.

24. A method of establishing initial therapy parameters of an implantable medical device comprising the steps of:
    (a) implanting at least one lead having a distal end, wherein the distal end of the lead is near at a predetermined portion of a body;
    (b) coupling a proximal end of the lead to an external neural stimulator;
    (c) establishing a bi-directional communications link between the external neural stimulator and a programmer;
    (d) programming the external neural stimulator therapy parameters with the programmer, the programming comprising:
        (i) providing initial therapy parameters to the external neural stimulator; and
        (ii) providing configuration information for a type of implantable neural stimulator that is to be programmed; and
    (e) providing final therapy parameters to the programmer from the external neural stimulator, whereby the programmer may then program an implantable neural stimulator using the final therapy parameters.

25. The method as claimed in claim 24, further comprising the step of:
    (f) adjusting the therapy parameters of the external neural stimulator using the programmer.

26. The method as claimed in claim 24, wherein the step of programming is performed via telemetry.

27. The method as claimed in claim 24, wherein the step of programming is performed using a physician programmer.

28. The method as claimed in claim 24, wherein the step of programming is performed using a patient programmer.

29. The method of claim 24, wherein the establishing in (c) comprises:
   (i) establishing a first RF leg of the bi-direction communication link between the programmer and a remote telemetry unit; and
   (ii) establishing a second RF leg of the bi-directional communication link between the remote telemetry unit and the external neural stimulator.

30. A medical system for providing electrical treatment therapy to a patient comprising in combination:
   at least one implantable lead delivering treatment therapy to the patient;
   an external neural stimulator having a first interface for coupling to the implanted lead for providing stimulation energy to the lead and a first bi-directional communications interface;
   an implantable neural stimulator capable of being implanted within a body of a patient and having an second interface for coupling to the implanted lead for providing stimulation energy to the lead and a second bi-directional communications interface;
   a physician programmer having a first user interface to allow entry of therapy parameters by a user and a third bi-directional communications interface for communicating with the external and implantable neural stimulators to enable the physician programmer to program the external and implantable neural simulators with the therapy parameters and to enable the external and implantable neural stimulators to provide therapy parameter settings back to the physician programmer, wherein the physician programmer is further configured to provide to the external neural stimulator configuration information for a type of the implantable neural stimulator that is to be implanted; and
   a patient programmer having a second user interface to allow entry of therapy parameters by a user and a fourth bi-directional communications interface for communicating with the external and implantable neural stimulators to enable the patient programmer to program the external and implantable neural simulators with the therapy parameters and to enable the external and implantable neural stimulators to provide therapy parameter settings back to the patient.

31. The medical system as claimed in claim 30, wherein the third bi-directional communications interface enables the physician programmer to provide to the external neural stimulator configuration information for a type of the implantable neural stimulator that is to be implanted.

32. The medical system as claimed in claim 30, wherein the third bi-directional communications interface enables the physician programmer to provide the external neural stimulator with upgraded computer executable instructions.

33. The medical system as claimed in claim 30, wherein the third bi-directional communications interface enables the physician programmer to provide the implantable neural stimulator with upgraded computer executable instructions.

34. The medical system as claimed in claim 30, wherein therapy parameter setting information is selected from the group consisting of stimulation frequency, stimulation pulse amplitude, stimulation pulse width, and electrode configuration.

35. The medical system as claimed in claim 30, wherein the third bi-directional communications interface enables the external neural stimulator to provide information to the physician programmer, wherein the information is selected from the group consisting of parameter settings, patient diagnostic data, system diagnostic data, data on device usage, data regarding the last programmer/ENS session, the state of the device, configuration of the INS 210, and whether a valid communication channel exists.

36. The medical system as claimed in claim 30, wherein the third bi-directional communications interface enables the implantable neural stimulator to provide information to the physician programmer, wherein the information is selected from the group consisting of parameter settings, patient diagnostic data, system diagnostic data, data on device usage, data regarding the last programmer/ENS session, the state of the device, configuration of the INS 210, and whether a valid communication channel exists.

* * * * *